(12) United States Patent
Goldberg et al.

(10) Patent No.: US 6,506,205 B2
(45) Date of Patent: Jan. 14, 2003

(54) BLOOD CLOT FILTERING SYSTEM

(76) Inventors: Mark Goldberg, 15 Livingston Rd., Sharon, MA (US) 02067; Ron Mallick, 1517 Lake Ave., Wilmette, IL (US) 60091; Lev Melinyshyn, 1018 Cambridge Dr., Buffalo Grove, IL (US) 60089

(*) Notice: Subject to any disclaimer, the term of this patent is extended or adjusted under 35 U.S.C. 154(b) by 40 days.

(21) Appl. No.: 09/788,878

(22) Filed: Feb. 20, 2001

(65) Prior Publication Data

US 2002/0116024 A1 Aug. 22, 2002

(51) Int. Cl.$^7$ ............................................... A61M 29/00
(52) U.S. Cl. ....................................................... 606/200
(58) Field of Search ......................... 623/1.11; 606/108, 606/159, 194, 198, 200, 191, 202, 113, 114, 127

(56) References Cited

U.S. PATENT DOCUMENTS

| | | |
|---|---|---|
| 3,654,773 A | 4/1972 | White |
| 3,810,367 A | 5/1974 | Peterson |
| 4,425,908 A | 1/1984 | Simon |
| 4,580,568 A | 4/1986 | Gianturco |
| 4,781,177 A * | 11/1988 | Lebigot ..................... 128/897 |
| 4,800,882 A | 1/1989 | Gianturco |
| 5,041,126 A | 8/1991 | Gianturco |
| 5,152,777 A | 10/1992 | Goldberg |
| 5,242,462 A | 9/1993 | El-Nounou |
| 5,282,824 A | 2/1994 | Gianturco |
| 5,314,444 A | 5/1994 | Gianturco |
| 5,324,304 A | 6/1994 | Rasmussen |
| 5,344,427 A | 9/1994 | Cottenceau |
| 5,375,612 A * | 12/1994 | Cottenceau et al. ........ 128/899 |
| 5,387,235 A | 2/1995 | Chuter |
| 5,456,713 A | 10/1995 | Chuter |
| 5,527,355 A | 6/1996 | Ahn |
| 5,562,724 A | 10/1996 | Vorwerk |
| 5,562,726 A | 10/1996 | Chuter |
| 5,693,084 A | 12/1997 | Chuter |
| 5,709,704 A | 1/1998 | Nott |
| 5,755,777 A | 5/1998 | Chuter |
| 5,836,969 A | 11/1998 | Kim |
| 5,843,170 A | 12/1998 | Ahn |
| 5,843,176 A | 12/1998 | Weier |
| 5,848,964 A | 12/1998 | Samuels |
| 5,853,420 A | 12/1998 | Chevillon |
| 5,968,071 A | 10/1999 | Chevillon |
| 5,984,947 A | 11/1999 | Smith |
| 6,007,558 A * | 12/1999 | Ravenscroft et al. ....... 606/194 |
| 6,013,093 A | 1/2000 | Nott |
| 6,080,178 A | 6/2000 | Meglin |
| 6,126,673 A | 10/2000 | Kim |
| 6,193,739 B1 | 2/2001 | Chevillon |
| 6,214,025 B1 | 4/2001 | Thistle |
| 6,217,600 B1 * | 4/2001 | DiMatteo .................... 606/191 |
| 6,231,589 B1 | 5/2001 | Wessman |
| 6,241,746 B1 | 6/2001 | Bosma |
| 6,251,122 B1 | 6/2001 | Tsukernick |
| 6,258,026 B1 | 7/2001 | Ravenscroft |
| 6,267,776 B1 | 7/2001 | O'Connell |
| 6,267,777 B1 | 7/2001 | Bosma |
| 6,273,900 B1 | 8/2001 | Nott |
| 6,325,815 B1 | 12/2001 | Kusleika |
| 6,328,755 B1 | 12/2001 | Marshall |
| 6,342,062 B1 | 1/2002 | Suon |
| 6,342,063 B1 * | 1/2002 | DeVries et al. ............. 606/200 |

OTHER PUBLICATIONS

Stent Placement for Caval and Tracheobronchial Stenoses, Saadoon Kadir, M.D. Current Practice of Interventional Radiology, B.C. Decker Inc., Philadelphia, PA.

U.S. patent application Ser. No. 09/863,660, filed May 22, 2001, Tsukernik.

* cited by examiner

Primary Examiner—Kevin T. Truong
Assistant Examiner—Vy Q. Bui
(74) Attorney, Agent, or Firm—Michael Best & Friedrich, LLC

(57) ABSTRACT

A blood clot filtering system including an anchor which is permanently affixed in a blood vessel, and a filter which is removably attached to the anchor.

45 Claims, 6 Drawing Sheets

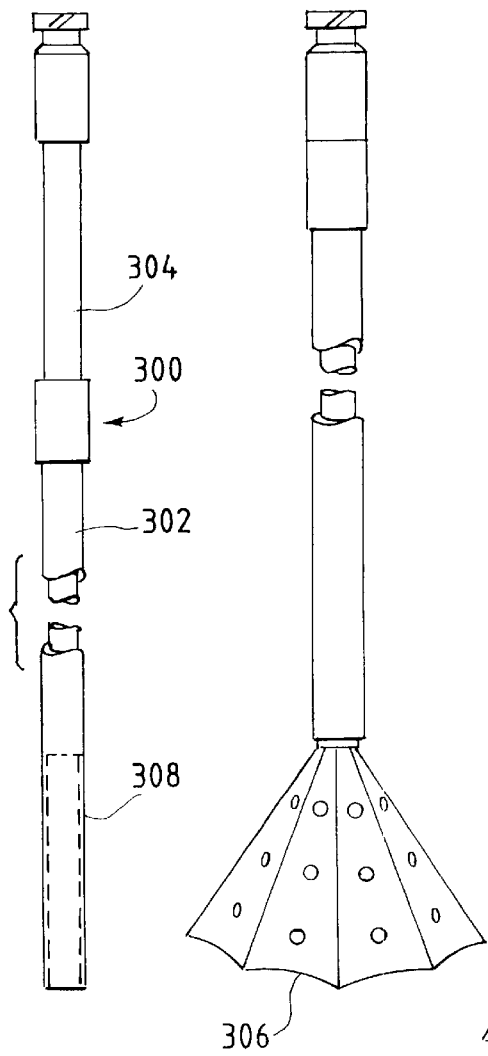
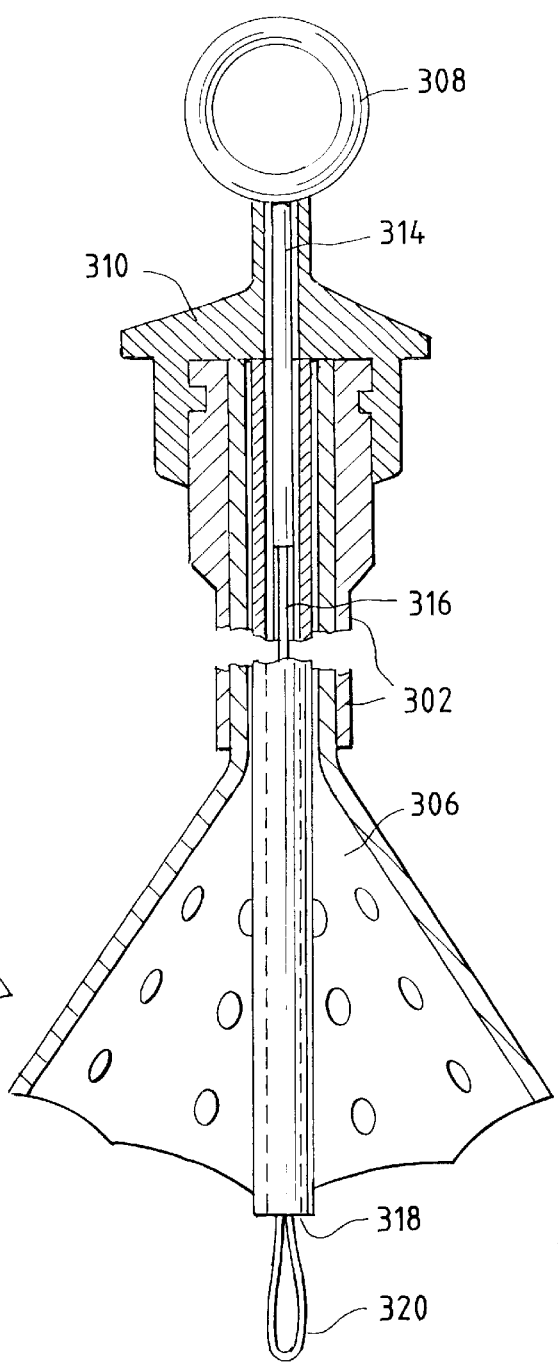
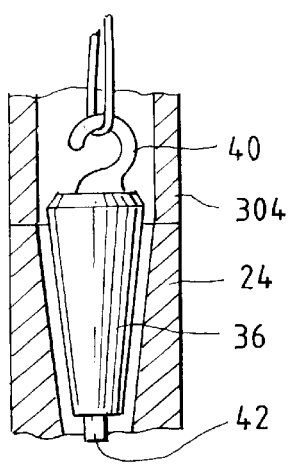

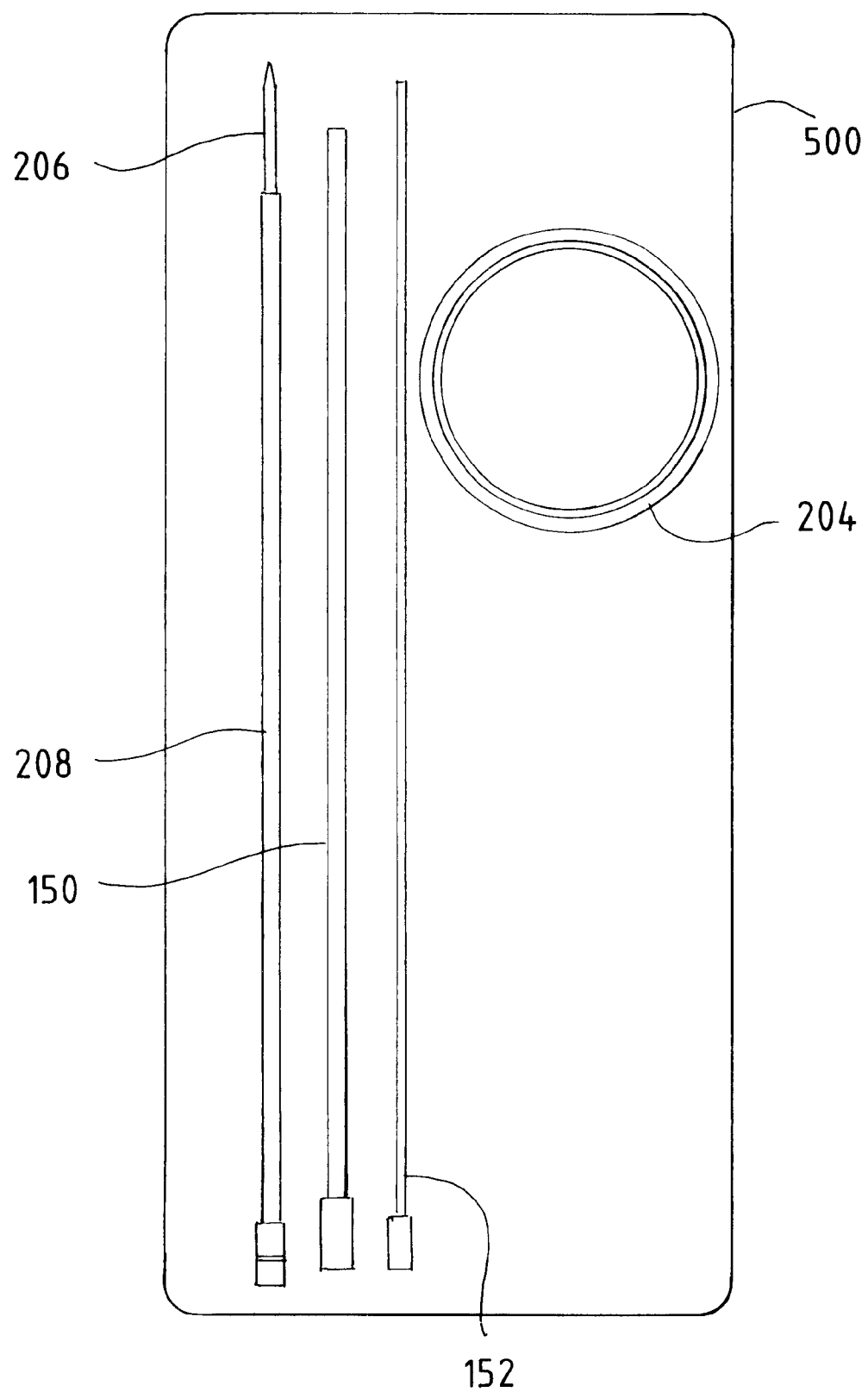

BLOOD CLOT FILTERING SYSTEM

BACKGROUND OF THE INVENTION

This invention relates generally to devices and methods for trapping blood clots and controlling embolization and some of the complications of thrombosis in blood vessels. More particularly, this invention relates to a blood filtering system that comprises two separable independent parts: a permanent anchor, and a filter removably attached to the anchor. The two parts of the system are attached in such a way that, once emplaced, the filter is continuously maintained along the central axis of the blood vessel to ensure that the filter operates at optimal efficiency. If and when it is necessary or desirable to remove the filter, it may readily be separated from the anchor and withdrawn, leaving a permanently attached anchor that does not interfere with blood flow within the blood vessel.

The presence of thrombus within the body's circulatory system presents significant health hazards, as manifested by potential acute venous thrombosis and chronic deep vein thrombosis. Acute venous thrombosis can lead to pulmonary emboli, a potentially lethal condition when an embolus travels into the pulmonary arteries. Currently, the most widespread treatment is the administration of systemic and oral anticoagulants such as heparin and coumadin, and thrombolytic agents such as TPA, urokinase and streptokinase.

Unfortunately, conventional drug therapy is ineffective or inappropriate for controlling emboli within the circulatory system of some patients. In particular, since most pulmonary emboli originate in veins of the lower limbs, pelvis or inferior vena cava, it has been recognized that life-threatening pulmonary emboli can be prevented from reaching the lungs by mechanically interrupting the inferior vena cava to filter out emboli.

Indications for introducing such filters in the inferior vena cava include:

a) Pulmonary embolism in patients with a high risk of internal bleeding, including those having surgery, anticipated surgery, recent trauma, cerebral hemorrhage or peptic ulcer disease who are not amenable to anticoagulant or thrombolytic therapy.

b) Recurrent pulmonary emboli notwithstanding anticoagulant therapy.

c) Patients showing large free-floating thrombi in the iliofemoral veins or inferior vena cava as identified with venography.

d) As prophylaxis against pulmonary emboli in older patients with high-risk conditions.

e) Disseminated thrombosis and profound thrombocytopenia in patients displaying heparin sensitivity.

f) Prevention of recurrent pulmonary emboli after pulmonary thrombolectomy.

In 1967–68, Eichelter and Schenk described an umbrella-like device which they introduced under local anesthesia into the femoral vein of dogs to filter emboli. Eichelter P. Schenk, W. G., Jr.: "A New Experimental Approach to Prophylaxis of Pulmonary Embolism". rev Surg 24:455–456 (Nov.-Dec.) 1967; Eichelter P. Schenk, W. G. Jr.: "Prophylaxis of Pulmonary Embolism." Arch Surg 97: 348–356 Aug. 1968. The Eichelter/Schenk device was constructed by making longtitudinal incisions circumferentially around a segment of a polyethylene tube, placing a tube of smaller diameter inside the larger tube and flaring the end protruding beyond the linear incisions. Light traction of the inner tube while holding the outer tube stable produced an umbrella-like structure. Unfortunately, this structure included numerous apertures for trapping stagnant blood and thereby promoting highly undesirable thrombosis and potential embolization.

Eichelter and Schenk made small incisions in the right femoral veins of the groins of the dogs used in the tests with the distal portion of the catheter tied into the femoral vein and the device open at a point lying distally to the renal veins. After a number of weeks, the device was collapsed and removed through a small incision. The embolization of trapped or attached emboli upon removal of the Eichelter/Schenk device precluded use of this device in humans.

A permanent implantable vena cava filter was developed by Mobin-Uddin in 1969, and described in U.S. Pat. No. 4,540,431. This filter was intended to be introduced through an incision in the jugular vein. The Mobin-Uddin filter was an umbrella-like structure having expanding ribs carrying sharpened points at their divergent ends which impaled the wall of the blood vessel when the filter was positioned at the desired location and permitted to expand into its operative structure. The Mobin-Uddin filter had a high occlusion rate and therefore was not widely used. Finally, even if initially properly implanted, these filters could come loose and migrate to either ineffective or dangerous and life-threatening locations in the vascular system.

The present invention solves the problems inherent in the prior art devices by providing a system establishing a quick, safe, and well-centered reliable emplacement of an effective emboli filter which is secure in the vessel until it becomes desirable or necessary to remove the filter. The present invention is particularly useful for placement in the inferior vena cava. The system may also be useful in filtering clots in other areas of the vascular anatomy.

SUMMARY OF THE INVENTION

It is therefore an object of the present invention to provide a two stage blood clot filtering system which can be quickly and safely emplaced within a blood vessel to efficiently trap emboli passing through the vessel.

Yet another object of the present invention is to provide an emplacable blood clot filtering system which, while maintaining patency, can provide either permanent or temporary protection from emboli in blood vessels.

It is yet another object of the present invention to provide a blood clot filtering system which can be emplaced through the femoral or internal jugular vein in a relatively simple procedure, during the course of which the system may be readily repositioned until optimally located in the vessel, and then positively fixed in that location for the desired, medically appropriate period.

A further object of the present invention is to provide a blood clot filtering system which can be steered through the vena cava under appropriate imaging techniques.

A still further object of the present invention is to provide an emboli or blood clot filter which, once emplaced, remains suspended along the longitudinal axis of the vessel as blood flows through the filter, minimizing endothelialization and vessel wall contact on the removable portion.

Another object of the present invention is to provide an emboli filter for emplacement in a blood vessel which can be permanently emplaced but which also can be readily removed when desired.

Yet another object of the present invention is to provide a blood clot filtering system for emplacement in blood vessels in which the patency is optimized and release of emboli into the bloodstream upon removal of the filter from the vessel is minimized.

Still another object of the present invention is to provide a blood clot filtering system including an anchor that is permanently emplacable in a blood vessel, and a removable filter attached to the anchor, in which endothelialization of the filter is minimized.

The present invention is therefore directed to a blood clot filtering system including an anchor which is permanently emplacable in a blood vessel and a blood clot filter removably attached to the anchor.

The anchor is radially self-expanding. It may be made of a metal spring wire material bent into a close zig-zag formation, with alternating zig and zag legs meeting at sharp angles at their distal and proximal vertices. At least two hooks may be provided respectively at least two distal vertices spaced equidistantly on a circle defined by the distal vertices.

The filter preferably includes two stages which cooperate to provide enhanced clot catching. The first stage comprises a series of distally projecting legs evenly spaced about the longitudinal axis of the filter, and the second stage comprises a series of generally radially projecting legs also evenly spaced about the longitudinal axis of the filter. The first stage may be also provided with a series of flexible filamentous tethers. The filter is removably attached to the anchor by way of these tethers. Finally, the filter may include a spring-loaded jaw at its proximal end. This jaw will retain both ends of each of the tethers when the tethers are attached to the anchor, but will release one end of each of the tethers in the process of removing the filter, leaving the anchor permanently fixed in place.

DESCRIPTION OF THE DRAWINGS

The objects and advantages of the present invention will be described with respect to the following figures in which:

FIGS. 9A and 9B illustrate a removal catheter including an umbrella which may be retracted and deployed from the catheter;

FIG. 10 is a cross-sectional view of the removal catheter of FIGS. 9A and 9B, including a snare handle mounted to the catheter;

FIG. 11 is an enlarged cutaway partial view of the end of the snare catheter abutting the jaw at the proximal end of the filter;

FIG. 14 is a diagrammatic representation of a blood clot filter emplacement kit containing the filtering system of the present invention.

DESCRIPTION OF THE INVENTION

Figure 1:
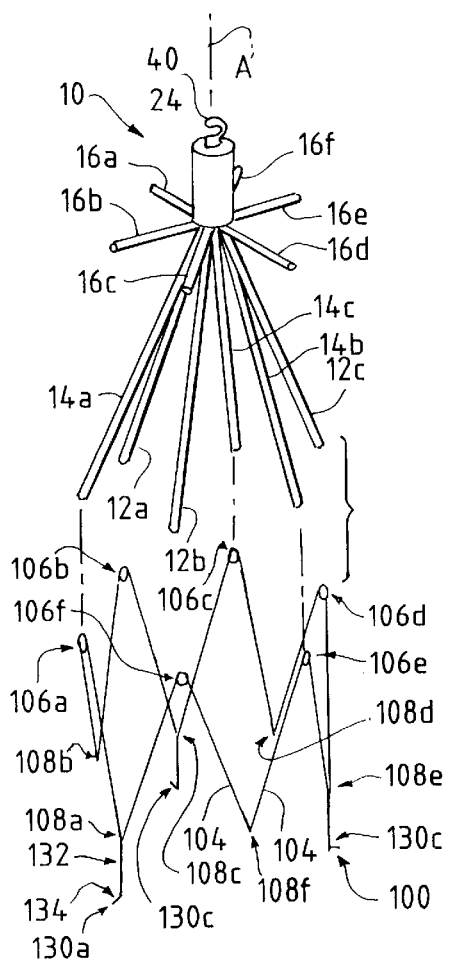
FIG. 1 is a perspective view of the filtering system of the present invention in which the filter and anchor of the system are separated for illustration purposes.

Turning first to FIG. 1, the blood clot filtering system 8 of the present invention is shown. The system includes a two stage filter 10 and an anchor 100. Two stage filter 10 comprises a series of distally projecting legs 12a–12c, evenly spaced about the central axis A of the device, constituting one portion of the first stage of the filter. While three distally projecting legs 12a–12c are illustrated, and constitute a preferred embodiment, four, five, six or more generally evenly spaced legs may be used. Also, the legs are shown in their fully open, non-in vivo position, at an angle of about 12° to longitudinal axis A, which is preferred. However, distally projecting legs 12a–12c may be at any angle ranging from about 2° to about 22° to axis A when at rest, before placement in an introducing catheter or emplacement in a blood vessel.

Distally projecting legs 12a–12c are made of a spring-like material which gives each leg rigidity along its longitudinal axis while permitting it to flex laterally, thereby enabling the filter to assume a fully closed configuration (FIG. 7) in which the legs are moved radially inward until they abut or nearly abut each other adjacent axis A of the filter. The distally projecting legs may be made from metal, for example, from stainless steel, nitinol, or Elgiloy® alloy (available from Egiloy L.P. of Elgin, Illinois, USA). In the illustrated embodiment, the distally projecting legs are made from stainless steel wire, and have a diameter of about 0.008 to 0.012 inch and preferably a diameter of about 0.010 inch.

The filter is intended to be in a fully closed configuration as it is inserted into or removed from a blood vessel, as described in more detail below. When the filter is deployed in a blood vessel (FIG. 8G), distally projecting legs 12a–12c will be flexed inwardly to a degree intermediate between the fully open and fully closed positions.

The first stage of the filter also includes a series of flexible filamentous tethers 14a–14c which, in the illustrated embodiment, are located between adjacent pairs of distally extending legs 12a–12c. Tethers 14a–14c may be round or flat and are made of a flexible, elastic material such as nitinol or stainless steel, or of nylon monofilament or other synthetic filamentous material. In the illustrated embodiment, the tether filaments are preferably flat and made of nitinol having a width of about 0.005 inch.

These tethers, which are attached to the filter and loop back from the anchor, providing filament loops, serve at least three purposes. The first is the attachment of the filter to the anchor in such a fashion that the filter will be centered and generally continuously maintained along the central longitudinal axis of a vessel in which the blood clot filtering system is deployed, insuring that the filter operates at peak efficiency. Second, the tethers permit the filter to be separated from the anchor when desired, so that the filter may be removed from the vessel. Finally, the filament loops of the tethers are an important feature of the first stage of the filter cooperating with legs 12a–12c. The tethers thus aid in first stage filtering by increasing the surface area coverage of the filter to improve the clot catching ability of the first stage of the filter which minimizes the likelihood of pulmonary embolization.

Filter 10 also includes a series of generally radially projecting legs 16a–16f which comprise the second stage of the filter. These legs are spaced generally evenly about the longitudinal or central axis A of the filter. Preferably, each of second stage legs 16a–16f is located in a plane defined by axis A and the proximal leg which generally bisects the interstice between each of distally projecting legs 12a–12c and its adjacent tethers 14a, 14b, and 14c. Although six such radially projecting second stage legs are shown in the illustrated embodiment, the number of legs may range from about 6 to 12.

In the illustrated embodiment, when the filter is in its fully open position, second stage legs 16a–16f extend proximally at an angle of about 70° to the central axis A of the filter, which is preferred. However, the radially projecting second stage legs may be at an angle from about 50° to 90° to central axis A. As in the case of the distally projecting legs, radially projecting second stage legs 16a–16f are made of a spring-like material which gives each leg longitudinal rigidity while permitting it to flex laterally. This enables the filter to assume a fully closed configuration (FIG. 7) in which the legs may be moved together until they abut or nearly abut each other adjacent axis A of the filter. As explained above, the filter is intended to be in this closed configuration as it is inserted or removed from a blood vessel.

Figure 8A:
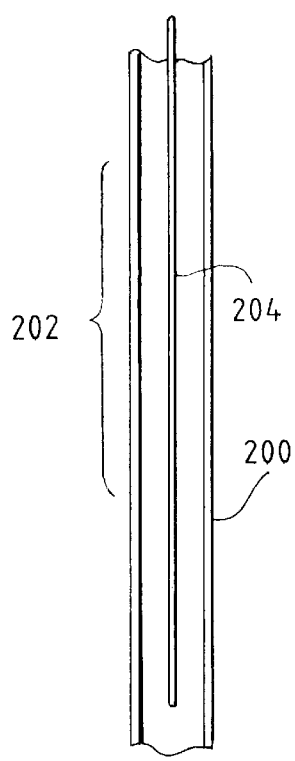
FIGS. 8A–8G illustrate diagrammatically the steps in emplacement of the filter system of the present invention in a blood vessel.
Figure 8B:
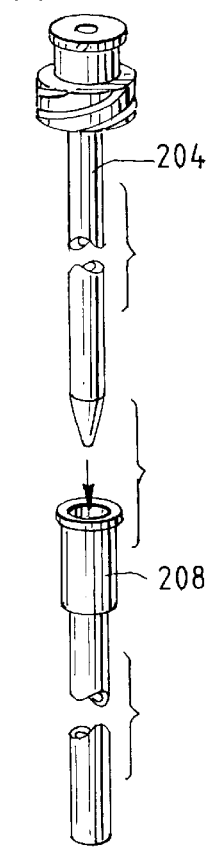
Figure 8C:
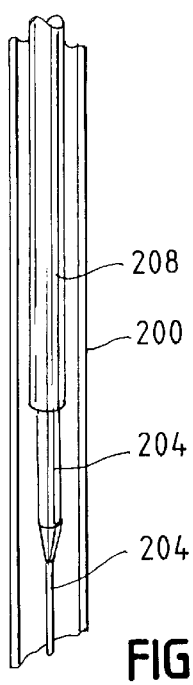
Figure 8D:
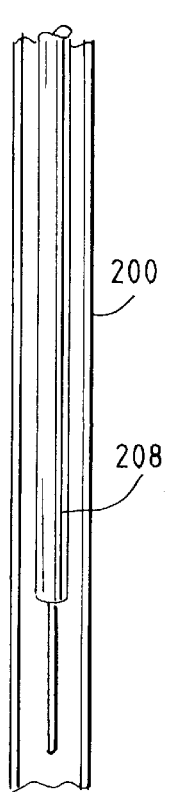
Figure 8E:
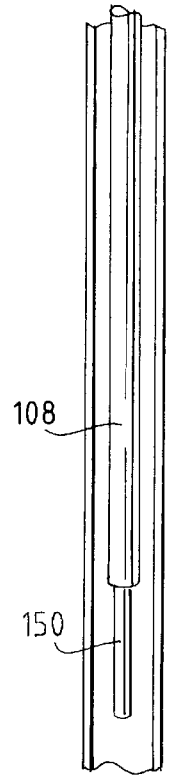
Figure 8F:
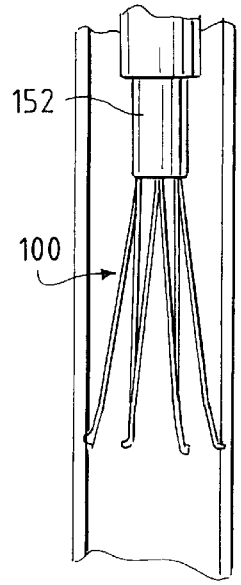
Figure 8G:
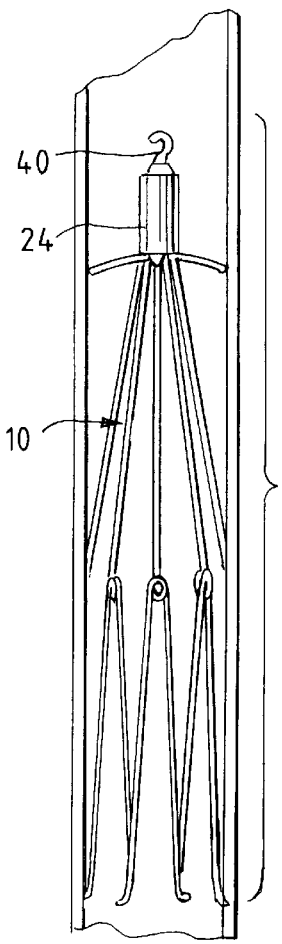

The radially projecting second stage legs will be flexed inwardly to a degree intermediate between the fully open and fully closed positions when the filter is deployed in a blood vessel (FIG. 8G). The radially projecting second stage legs may be made, for example, from stainless steel, nitinol or Elgiloy® alloy. In the illustrated embodiment, these legs are made from round stainless steel wire having a diameter of about 0.008 to 0.012 inch. Flat or round wire may be used, although round wire is preferred.

The first and second stages of filter 10 cooperate to provide enhanced clot catching. Thus, the first stage encounters and captures most clots while the second stage traps any emboli that might slip by the first stage, preventing emboli from proceeding beyond the filter.

Figure 2:
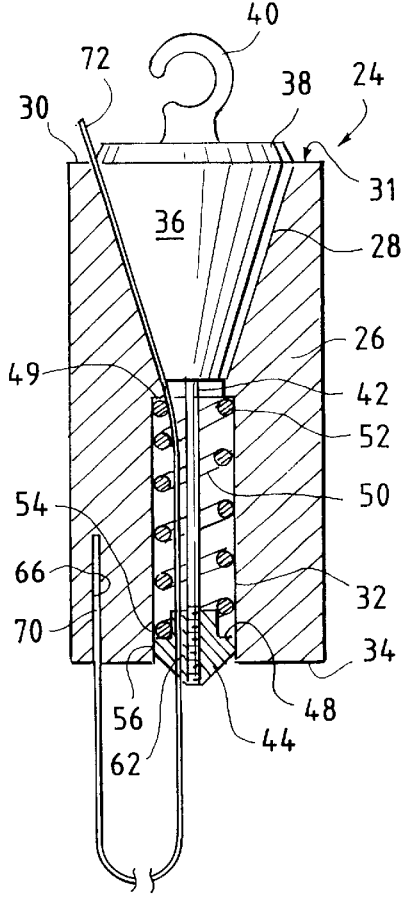
FIG. 2 is an enlarged cross-sectional view of the jaw at the proximal end of the filter of FIG. 1.

Filter 10 also includes a spring-loaded jaw 24 having an open hook 40 at its proximal end. law 24 is described in more detail in the discussion of FIG. 2 which follows.

FIG. 2 is an enlarged cross-sectional view of jaw 24 including a jaw body 26 having a truncated conical cavity 28, a proximal end 30, a distal end 34, and a bore 32 extending from the truncated distal end of cavity 28 to the distal end 34 of the jaw. A top truncated conical member 36 is shaped and sized to fit in conical cavity 28 with a portion 38 of the conical member protruding beyond the proximal end 30 of the body of the jaw encircled by an annular shoulder 31 at the proximal end of the jaw body. Hook 40 is attached to the protruding portion 38 of the conical member, centered on the longitudinal. axis of the jaw.

A rod 42 is affixed to the distal end of conical member 36 and extends distally therefrom, along the central axis of the conical member. A cap 44 is affixed to the distal end of rod 42. Cap 44 is cylindrically shaped and sized to fit snugly but slideably within bore 32, and has a smooth conical distal tip 46 and an annular shoulder 48 at its proximal end. Conical cavity 28 opens at its distal end into cylindrical bore 32. Since the truncated distal end of the conical aperture has a diameter less than that of the cylindrical bore, an annular shoulder 49 is formed at this intersection. Encircling rod 42 is a compression spring 50 with the proximal end 52 of the spring resting on annular shoulder 49 at the intersection of the conical aperture and the cylindrical bore and the distal end of the spring 54 resting on shoulder 48 of the cap. Thus, compression spring 50 is compressed and confined in bore 32 between shoulders 48 and 49, maintaining conical member 36 in cavity 28. In a preferred embodiment, silicone grease may be placed in bore 32 to minimize sticking in the jaw over time. Alternatively, the inner surface of the bore and/or the outer surface 56 of the cap may be coated with polytetrafluoroethylene (Teflon®) or another low resistance or surface-modifying material which minimizes sticking.

Cylindrical cap 44 includes longitudinal bores 62 generally evenly spaced around rod 42 that pass through the cap. The number of bores 62 correspond to the number of tethers in the filter. Thus, although one throughbore is shown in the cutaway representation of jaw 24 in FIG. 2, in the illustrated embodiment of the invention there are three longitudinal throughbores 62 at roughly 120° spacings about the central axis of the cylindrical cap corresponding to tethers 14a, 14b, and 14c. Additionally, the body of the jaw includes a like number of blind longtitudinal bores 66 extending proximally from the distal end 34 of the body member and evenly spaced about the longitudinal axis of the jaw. (As in the case of throughbores 62, only one blind bore is shown in the cutaway representation of jaw 24).

FIG. 2 shows one of the three tethers (14c) which, for illustration purposes, is foreshortened. One end 70 of the filament of tether 14c is fixed in bore 66 by conventional means such as swaging or laser welding. After being passed through the anchor, the tether filament is passed through bore 62 past the individual coils of compression spring 50, and out along the surface of conical cavity 28 with the distal tip 72 of the tether filament at the proximal end 30 of the body of the jaw. Conical member 36 which is firmly resiliently seated in cavity 28 under the biasing force of spring 50 thus locks the tether filament between the abutting surfaces of cavity 28 and conical member 36. When a force is applied proximally to hook 40 while the jaw is restrained along shoulder 31, spring 50 is compressed, unseating conical member 36 and causing a gap to open up between the two abutting surfaces, releasing or unlocking tether 14c. When it is released, the tether is free to pass back out through the coils of the spring and bore 62, so that the two stage filter 10 may be detached from anchor 100 and withdrawn proximally from the vessel in which it was emplaced. Jaw 24 in cooperation with tethers 14a, 14b, and 14c therefore makes it possible to simply and efficiently separate filter 10 from anchor 100, in a procedure as described below.

Figure 3:
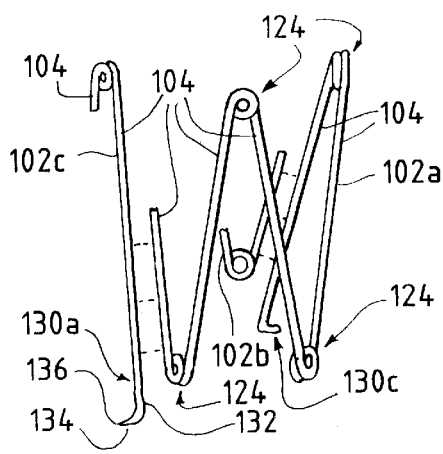
FIG. 3 is perspective view of the anchor of the filtering system of the present invention.

Anchor 100 is self-expanding and includes a series of joined wire segments 102a, 102b, and 102c (FIG. 3) which are each bent into a close zig-zag formation, with alternating zig and zag legs 104 meeting at sharp angles at their vertices. As shown in the figures, the vertices preferably present a rounded, rather than a pointed tip. While the number of zig and zag legs and hence vertices may vary, in a preferred embodiment, as illustrated in FIG. 1, there are twelve zig and zag legs, resulting in six proximal vertices 106a–106f, and six distal vertices, 108a–108f. In practice, the number of zig and zag legs and hence vertices may range from six to eighteen. As illustrated in FIG. 3, anchor 100 may be made of a series of separate wire segments which are spot or laser welded together as indicated in dashed lines. Of course, the anchor may be made of a single piece of wire, if desired.

The wire or wires from which filter 100 is made are a metal spring wire material, such as stainless steel or nitinol. In the illustrated embodiment, stainless steel wire is used which is presently preferred. The use of spring material and the zig-zag structure permits the. anchor to be squeezed radially together, so that it takes up a minimal amount of space radially, to facilitate emplacement of the anchor, as described in more detail below.

Spring hinges or "safety pin curls" 124 are formed at each of the vertices, 106a–106f and 108a–108f. These spring hinges are preferred, but may be dispensed with in a less preferred embodiment of the invention. The spring hinges make for an enhanced radially outward spring force which improves retention of the anchor in a blood vessel. Also, it is preferred that alternate vertices be offset from each other in order to minimize interference between adjacent hinges when the anchor is in the fully closed position. This offsetting affects the manner in which the safety pin curls contact each other when the anchor is collapsed into the introducing catheter. If all pairs of zig zag legs were equal in length, the curls would "stack up" and take more radial space when collapsed. By alternating the leg lengths, and therefore the positions of the vertices, the curls are staggered and thus require less radial space when the anchor is in the fully closed position.

Three hooks 130a, 130b, and 130c are provided respectively at distal vertices 108a, 108c, and 108e. At least two such hooks must be present, and preferably from two to six hooks will be used. In all cases, the hooks are preferably spaced equidistantly along the circle defined by the distal vertices. In the illustrated embodiment, the hooks are formed from protruding end portions of the wire segments from which the anchor is made. Each of the hooks includes a longtitudinal portion 132 and a radial portion 134. Radial portion 134 is preferably sharpened to a point 136 (FIG. 3). Thus, when the anchor is emplaced in a blood vessel and permitted to expand outwardly under the spring force produced at the vertices of the zig-zag segments, the radially outward force seats and retains the anchor in place. Additionally sharpened points 136 engage the vessel wall, further fixing the anchor in place.

Surface modifiers for reducing or preventing endothelialization, such as Rapamune® (rapamycin) which is available from Wyeth-Ayerst Laboratories Division of American Home Products or Taxol® (paclitaxil) which is available from Bristol-Myers Squibb, may be applied to every part of the filtering system except the anchor, including the filter legs, tethers and jaw. Such surface modifiers might not be applied to the anchor because limited endothelialization on the anchor surfaces is desirable to cover those surfaces thereby enhancing anchoring and minimizing contact between the blood flowing past the anchor and the metal from which the anchor is formed.

Figure 4:
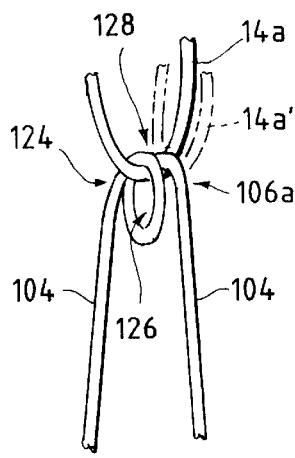
FIG. 4 is an enlarged view of one of the curls at a proximal vertex of two zig-zag legs of the anchor showing a tether filament passing through the loop in the curl.

In assembling the filter to the anchor, tethers 16a–16c are passed through the three vertices 106a, 106c, and 106e. When safety pin curls 124 are used, it is important, as illustrated in the enlarged partial view of FIG. 4, that the tethers (e.g., tether 14a in FIG. 4) pass through the loops 126 of the safety pin curls, and not in the space 128 between the abutting coils, as shown in the broken line representation of the tether 14a. In the latter case, the filament could be pinched between the abutting coils, which could interfere with separation of the filter from the anchor.

Figure 5:
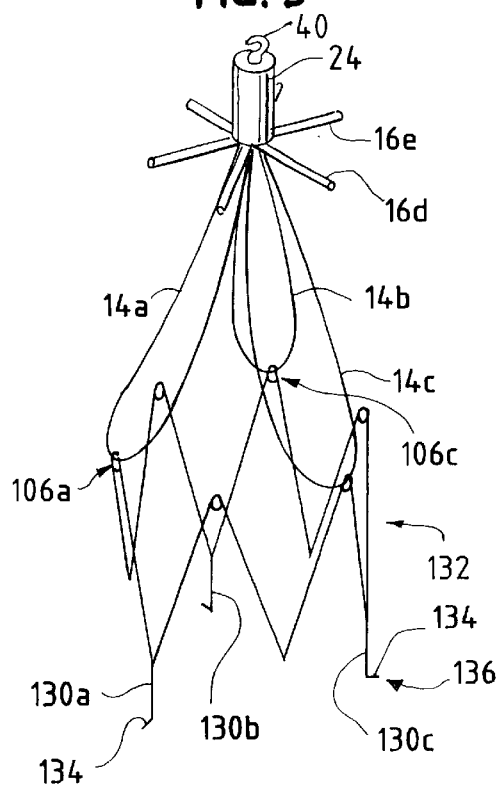
FIG. 5 is a perspective view of the assembled filtering system of the invention showing the filaments of the filter tethers passing through loops at alternating proximal vertices.

In order to clarify the way in which the filter is assembled to the anchor by way of the tethers, the assembled system is shown in FIG. 5 with the anchor fully expanded and with its three hooks 130a, 130b, and 130c resting on a horizontal surface 132. The filter is lowered somewhat with respect to the anchor to cause the tethers to balloon outwardly for illustration purposes. Thus, it can be seen in this figure that the filaments of tethers 14a, 14b, and 14c extend from jaw 24 respectively through the curl loops at vertices 106a, 106c, and 106e, and back up into the jaw to be removably held therein, in the manner described above with respect to the structure and operation of the jaw. When the system is deployed in a vessel, the anchor is compressed radially inward as it abuts the walls of the vessel, as are the legs of the filter. In this in vivo configuration, the filaments of the tethers will be elongated and drawn more closely together, generally as shown in FIG. 8G, which is discussed below.

Figure 6:
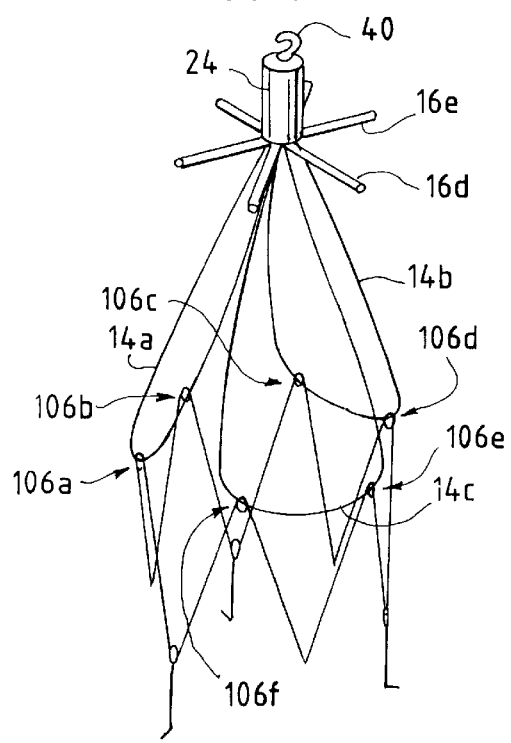
FIG. 6 is a perspective view of the assembled filtering system of the invention showing the filaments of the filter tethers passing through adjacent pairs of proximal vertices.

FIG. 6 shows an alternative way in which the filter may be assembled to the anchor by way of the tethers. In this figure, tether filaments 14a, 14b, and 14c pass from the jaw through adjacent pairs of curl loops at adjacent vertices 106a and 106b, 10c and 106d, 106e and 106f, and back to the jaw.

Figure 7:
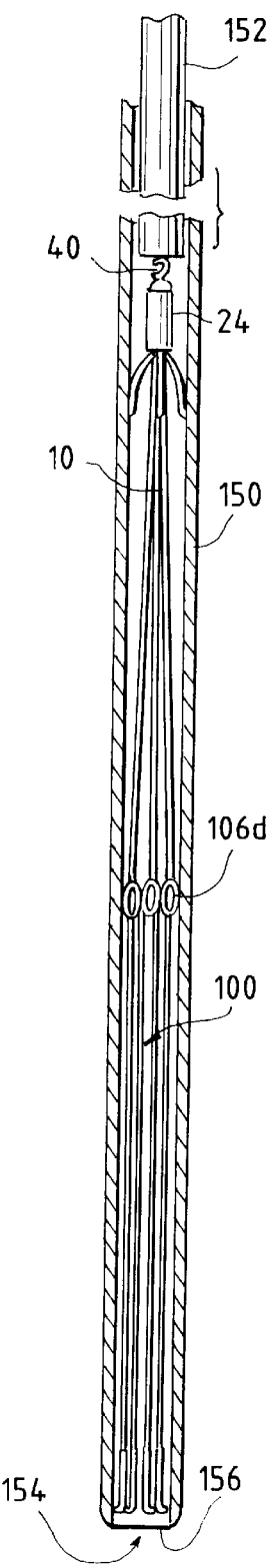
FIG. 7 is an elevation view of a flexible introducing catheter partially cut away to show the assembly of the filter and anchor collapsed radially and positioned in the catheter.

Before deploying the filter system of the present invention, the assembly of the filter and anchor are collapsed radially and placed in a flexible introducing catheter 150, as illustrated in FIG. 7. In the illustrated embodiment, catheter 150 is shown, cut away in order to make it possible to view the assembled filter and anchor in the catheter. Also shown in this figure is a pusher 152, which is used to deploy (by pushing) the attached catheter and anchor from the annular aperture 154 at distal end 156 of the catheter when the catheter is positioned at the location within the blood vessel at which it is intended to be used.

Actual emplacement of the filter system of the present invention is shown in FIGS. 8A–8G which illustrate an internal jugular approach. It is important to note that this system can be adapted to a femoral approach as well. Turning first to FIG. 8A, a portion of the vena cava vessel 200 is illustrated diagramatically at the desired implant site 202. As can be seen in this figure, a guidewire 204 has been inserted in the vena cava so that it extends beyond the implant site. Next, as shown in FIGS. 86 and 8C, a conventional dilator 206 and sheath 208 assembly is passed over the guidewire and advanced therealong until the sheath and dilator reach beyond the implant site (FIG. 8C).

Next, dilator 206 and guidewire 204 are withdrawn and sheath 208 is flushed with heparinized saline to prevent thrombus formation in the sheath. A venacavogram is then obtained by injecting a contrast medium through the sheath 208 so that the position of the sheath can be adjusted to optimize the later positioning of the anchor and filter. This leaves sheath 208 deployed on guidewire 204, as illustrated in FIG. 8D.

Now, introducing catheter 150, with the preloaded filter/anchor assembly as illustrated in FIG. 7, is flushed with heparinized saline, and then passed through sheath 208, until the introducing catheter protrudes beyond the end of the sheath, as illustrated in FIG. 8E. Now, pusher 152 (FIG. 7) is inserted until it meets the loaded filter system and held stationary in that position while the introducing catheter is slowly withdrawn, which deploys first the anchor, as shown in FIG. 8F, and then the entire filter system 8, as illustrated in FIG. 8G.

As noted above, one advantage of the present invention is that it makes it possible to easily remove the filter, if and when desired. As will be explained in greater detail below, removal generally entails: 1) restraining shoulder 31, 2) snaring hook 40, 3) pulling up upon the hook to open jaw 24 and release the tethers, making it possible to separate the filter from the anchor, and 4) withdrawing the filter from the vessel, leaving the anchor in place. When the filter is removed, the design of the filter, particularly the longitudinally rigid, smooth surfaced legs of the first and second stages of the filter, act as pins which minimize contact and resistance during withdrawal. Also, while the filter is held in place by the firmly attached anchor, the filament legs have little if any contact with the wall of the vena cava.

For example, as shown in FIGS. 9A and 9B, a snare or removal catheter 300 is shown having an outer sleeve 302 and an inner hollow umbrella shaft 304. An umbrella 306 is collapsed and resting in the distal end 308 of the removal catheter. Thus, when the sleeve 302 is retracted, umbrella 306 is deployed and opened, as in FIG. 7B.

Turning now to FIG. 10, further details of the snare catheter are illustrated. As shown in this figure, the snare catheter includes a pull ring 308 at its proximal end, mounted to a snare handle 310 which is fit onto the proximal end 312 of the snare catheter. The pull ring has a distally directed shaft 314 with a snare wire 316 which is attached at one end to shaft 314, and passes down through catheter and out of its distal end 318, where it forms a snare loop 320 before it passes back up through the shaft and is attached at its other end to shaft 314. Snare loop 320 may be angled up to 900 from the longitudinal axis of the snare catheter to make it easier to use in snaring hook 24 (as discussed below). Also, the size of the snare loop may be made adjustable as needed.

Thus, when it is desired or necessary to remove a previously emplaced filter, the removal catheter is passed down through the vessel in which the filter system of the invention is emplaced until snare loop 320 latches onto hook 40, with the distal end 318 of shaft 304 abutting the annular shoulder 31 of the jaw (FIG. 11). Umbrella sleeve 302 is then retracted to deploy umbrella 306 in the vessel. Once the snare loop, sleeve and umbrella are in this position, the user pulls distally on the snare ring to retract snare loop 320, pulling on hook 40, and releasing the tethers so that the snare catheter and filter may be withdrawn through the vessel leaving the anchor in place. Umbrella 306, which is optional, will catch any clots which may be freed during the procedure, which otherwise could cause the clinical manifestation of a pulmonary embolus. The umbrella should be permeable to prevent obstruction of normal blood flow. This may be achieved, for example, by providing holes 307, as shown in the illustrated embodiment and/or the umbrella may be made of a fine mesh material (not shown).

Figure 12:
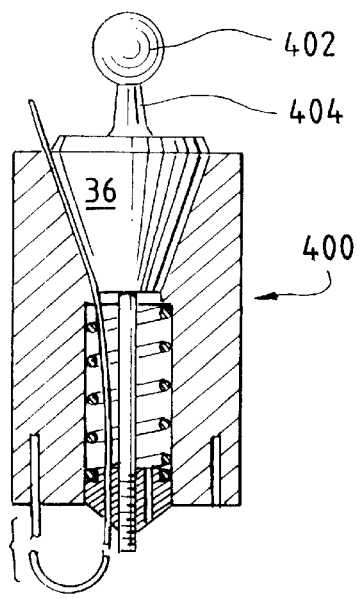
FIG. 12 illustrates an alternative design of the jaw depicted in FIG. 2 in which the proximal hook is replaced by a ball.
Figure 13A:
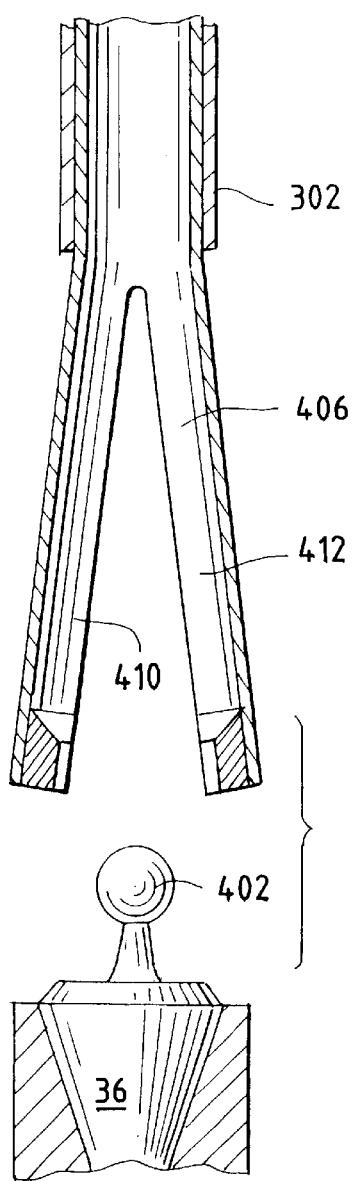
FIGS. 13A and 13B illustrate the capture of a ball at the proximal end of the jaw and the application of a distally directed force for releasing the tether filaments and removing the filter from a blood vessel in which it was previously deployed.
Figure 13B:
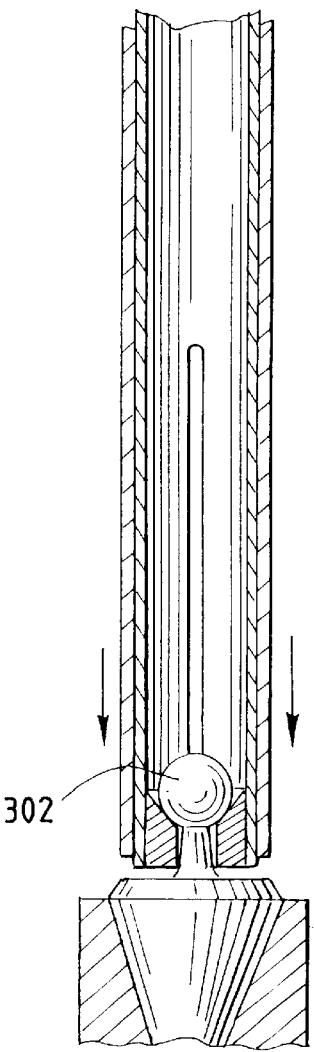

An alternate embodiment of the invention as it applies to the removal of the filter system is illustrated in FIGS. 12 and 13. Thus, a jaw 400 is illustrated in FIG. 12. As is apparent from FIG. 12, this jaw corresponds to that of FIG. 2, except that hook 40 has been replaced by a ball 402 attached to the distal end of top conical member 36 by way of a pedestal 404. A locking sleeve 406, as shown in FIG. 13A, is provided at the end of the removal catheter. The locking sleeve is shown in this figure in its extended position, with a pair of clasping jaws 410 and 412 in their open position, juxtaposed just above ball 402 of the jaw. Thus, turning to FIG. 13B, locking sleeve 406 has been moved to its fully retracted position, withdrawing the clasping jaws 410 and 412 into the catheter, causing them to pivot radially inward and to lock upon ball 402. As in the above discussion of FIGS. 10 and 11, the catheter is then withdrawn, causing jaw 400 to release the tethers so that the filter may be removed from the blood vessel.

Finally, a blood clot filter emplacement system is illustrated diagrammatically, in kit form, in FIG. 14. This figure includes a container 500, containing an introducing catheter 150 with a preloaded filtering system, generally as illustrated in FIG. 7, in which the filter is oriented for emplacement from above through an upper central vein which could include the internal jugular, subclavian or brachial vein. The position of the filter in the introducing catheter could be reversed for emplacement from below, through the femoral vein. Container 500 also includes a sheath 208 with a dilator 206 contained therein, a coiled guidewire 204, and a pusher 152. The blood clot filtering system of the present invention may be conveniently provided to a user in this kit form to facilitate the emplacement procedure.

There have been described herein a blood clot filtering system and a method for its use free from the shortcomings of the prior art. It will be apparent to those skilled in the art that modifications may be made without departing from the spirit and scope of the invention. Accordingly, it is not intended that the invention be limited except as may be necessary in view of the appended claims.

What we claim is:

1. A blood clot filtering system comprising:
   a tether;
   an anchor including means for permanently emplacing the anchor in a blood vessel;
   a blood clot filter separate from the anchor and removably attached to the anchor by the tether; and
   a means for releasing the tether from the anchor.

2. The blood clot filtering system of claim 1 in which the anchor is radially self-expanding.

3. The blood clot filtering system of claim 2 in which the anchor is made of a metal spring wire material bent into a close zig-zag formation, with alternating zig and zag legs meeting at sharp angles at their distal and proximal vertices.

4. The blood clot filtering system of claim 3 in which there are 6–18 zig and zag legs.

5. The blood clot filtering system of claim 3 in which the anchor is made of a series of separate wire segments.

6. The blood clot filtering system of claim 3 in which the wire spring material is chosen from the group consisting of stainless steel and nitiniol.

7. The blood clot filtering system of claim 3 in which spring hinges are formed at each of the vertices.

8. The blood clot filtering system of claim 7 in which the spring hinges are offset from each other.

9. The blood clot filtering system of claim 3 in which at least two hooks are provided respectively at at least two distal vertices space equidistantly on a circle defined by the distal vertices.

10. The blood clot filtering system of claim 5 in which hooks are provided at at least two distal vertices and the hooks are formed from protruding end portions of the separate wire segments.

11. The blood clot filtering system of claim 1 in which the blood clot filter includes two stages which cooperate to provide enhanced clot catching.

12. The blood clot filtering system of claim 11 in which the first stage comprises a series of distally projecting legs evenly spaced about the longitudinal axis of the system.

13. The blood clot filtering system of claim 12 in which three or more evenly spaced distally projecting legs are provided.

14. The blood clot filtering system of claim 12 in which the distally projecting legs are made of a spring-like material that gives each leg rigidity along its longitudinal axis while permitting each leg to flex laterally.

15. The blood clot filtering system of claim 14 in which the distally projecting legs, in their fully open, non-in vivo position, are at an angle ranging from about 2° to about 22° to the longitudinal axis of the system.

16. The blood clot filtering system of claim 14 in which the distally projecting legs, in their fully open, non-in vivo position, are at an angle of about 12° to the longitudinal axis of the system.

17. The blood clot filtering system of claim 14 in which the distally projecting legs are made from stainless steel wire having a diameter of about 0.008 inch to 0.012 inch.

18. The blood clot filtering system of claim 12 in which the first stage also comprises a plurality of flexible filamentous tethers.

19. The blood clot filtering system of claim 18 in which the flexible filamentous tethers cooperate with the distally projecting legs to aid in catching clots.

20. The blood clot filtering system of claim 18 in which the tethers are located between adjacent pairs of distally extending legs.

21. The blood clot filtering system of claim 18 in which the tethers are made of a material chosen from the group consisting of nitinol, stainless steel, and synthetic filamentous materials.

22. The blood clot filtering system of claim 18 in which the tethers are flat are made from nitinol, and have a width of about 0.005 inch.

23. The blood clot filtering system of claim 11 in which the second stage comprises a series of generally radially projecting legs generally evenly spaced about the longitudinal axis of the system.

24. The blood clot filtering system of claim 23 in which each of the second stage legs is positioned so that, in the deployed filter, it will generally bisect the space between each of the distally projecting legs and its adjacent tether.

25. The blood clot filtering system of claim 23, in which about 6 to 12 radially projecting second stage legs are provided.

26. The blood clot filtering system of claim 23 in which the radially projecting legs are made of a spring-like material that gives each leg rigidity along its longitudinal axis while permitting each leg to flex laterally.

27. The blood clot filtering system of claim 23 in which the radially projecting legs, in their fully open, non-in vivo position, are at an angle ranging from about 50° to about 90° to the longitudinal axis of the filter.

28. The blood clot filtering system of claim 23 in which the radially projecting legs, in their fully open, non-in vivo position, are at an angle of about 70° to the longitudinal axis of the filter.

29. The blood clot filtering system of claim 23 in which the radially projecting legs are made from stainless steel wire having a diameter of about 0.008 inch to 0.012 inch.

30. The blood clot filtering system of claim 23 in which the radially projecting legs are made from round wire.

31. The blood clot filtering system of claim 1 in which the surfaces of the anchor are coated with a surface modifier for reducing or preventing endothelializtion.

32. A blood clot filtering system comprising:
   an anchor including means for permanently emplacing the anchor in a blood vessel, the surfaces of the anchor being coated with a surface modifier for reducing or preventing endothilialization where the surface modifier is chosen from the group consisting of rapamycin and paclitaxil; and
   a blood clot filter removably attached to the anchor.

33. The blood clot filtering system of claim 18 in which the filter includes means for removably retaining at least one end of each of the flexible filamentous tethers.

34. The blood clot filtering system of claim 33 in which the retaining means comprises a spring-loaded jaw.

35. A blood clot filtering system comprising:
   an anchor including means for permanently emplacing the anchor in a blood vessel, with the anchor being made of a metal spring wire material bent into a closed zig-zag formation, with alternating zig and zag legs meeting at sharp angles a their distal and proximal vertices;
   a blood clot filter including two stages which cooperate to provide enhanced clot catching, in which the first stage includes a series of distally projecting legs spaced about the longitudinal axis of the system, a series of flexible filamentous tethers removably attaching the filter to the anchor, and means for removably retaining at least one end of each of the flexible filamentous tethers,
   in which the retaining means comprises a spring-loaded jaw, one end of each tether is fixed to the jaw, and the opposite end passes through a proximal vertex of the anchor and back to the jaw where it is removably held so that, when the tether end is released from the jaw, the filter may be detached from the anchor.

36. The blood clot filtering system of claim 34 in which the spring-loaded jaw includes a conical cavity and a conical member shaped and sized to seat displaceably therein under a spring force provided by the jaw, with at least a portion of the outer surface of the conical member abutting at least a portion of the inner surface of the conical cavity, whereby at least one end of each of the flexible filamentous tethers is removably retained between the abutting surfaces of the conical cavity and the conical member.

37. The blood clot filtering system of claim 36 in which one end of each of the flexible filamentous tethers is removably retained between the abutting surfaces of the conical cavity and the conical member and the other end of each of the flexible filamentous tethers is fixed to the jaw.

38. The blood clot filtering system of claim 35 in which the anchor is made of a metal spring wire material bent into a close zig-zag formation, with alternating zig and zag legs meeting at sharp angles at their distal and proximal vertices and the tethers pass through selected ones of the proximal vertices.

39. The blood clot filtering system of claim 38 in which spring hinges are formed at the vertices and the tethers pass through the spring hinges at the proximal vertices.

40. The blood clot filtering system of claim 34 in which movable abutting surfaces of the jaw are coated with a material which minimizes sticking.

41. The blood clot filtering system of claim 39 in which the tethers each pass through more than one of the spring hinges.

42. The blood clot filtering system of claim 40 in which the coating is chosen from the group consisting of silicone grease and polytetrafluoroethylene.

43. The blood clot filtering system of claim 1 including a plurality of tethers.

44. A blood clot filtering system comprising:
   an anchor including means for emplacing the anchor in a blood vessel;
   a blood clot filter;

flexible filamentous tethers located between the anchor and the filter removably attaching the anchor to the filter; and means for releasing the tether from the anchor.

45. A blood clot filtering system comprising:

an anchor including means for emplacing the anchor in a blood vessel; and a blood clot filter removably attached to the anchor;

the filter further including a series of spring-like distally diverging legs each having rigidity along its longitudinal axis but being able to flex laterally; and a series of flexible filamentous tethers attaching the anchor and the filter, and the tethers being attached adjacent the proximal ends of the distally diverging legs.

\* \* \* \* \*